（12） United States Patent
Lin et al.

(10) Patent No.: US 12,397,172 B2
(45) Date of Patent: Aug. 26, 2025

(54) CHIP PAD DECOMPRESSION STRUCTURE

(71) Applicant: Ghi Fu Technology Co, Ltd., Changhua County (TW)

(72) Inventors: Li-Chi Lin, Changhua County (TW); Yi-Ying Lin, Changhua County (TW)

(*) Notice: Subject to any disclaimer, the term of this patent is extended or adjusted under 35 U.S.C. 154(b) by 408 days.

(21) Appl. No.: 18/151,472

(22) Filed: Jan. 9, 2023

(65) Prior Publication Data

US 2023/0226371 A1 Jul. 20, 2023

(30) Foreign Application Priority Data

Jan. 18, 2022 (TW) .................................. 111102024

(51) Int. Cl.
*A61N 5/06* (2006.01)

(52) U.S. Cl.
CPC .... *A61N 5/0625* (2013.01); *A61N 2005/0645* (2013.01); *A61N 2005/066* (2013.01)

(58) Field of Classification Search
CPC .......... A61N 5/0625; A61N 2005/0645; A61N 2005/066; A61N 5/06–2005/073
See application file for complete search history.

(56) References Cited

U.S. PATENT DOCUMENTS

| | | | | |
|---|---|---|---|---|
| 11,837,513 | B2* | 12/2023 | Meier | G01N 27/28 |
| 2006/0235346 | A1* | 10/2006 | Prescott | A43B 3/36 |
| | | | | 602/2 |
| 2014/0303692 | A1* | 10/2014 | Pignatelli | A61N 5/0613 |
| | | | | 607/90 |
| 2018/0304094 | A1* | 10/2018 | Hicks | A61N 5/0616 |
| 2021/0020528 | A1* | 1/2021 | Meier | G01N 27/283 |
| 2021/0069489 | A1* | 3/2021 | Lawson | A61N 1/0484 |

FOREIGN PATENT DOCUMENTS

WO WO-2022036518 A1 * 2/2022

* cited by examiner

*Primary Examiner* — Jonathan T Kuo
(74) *Attorney, Agent, or Firm* — Bruce Stone LLP; Joseph A. Bruce

(57) ABSTRACT

A chip pad decompression structure includes a pad, a protective ring, a chip, and an upper lid. A middle of one side of the pad has a raised portion. Another side of the pad has a recess. The protective ring is disposed in the recess of the pad. The protective ring has a through hole. The chip is disposed in the through hole of the protective ring and located in the recess of the pad. The upper lid is configured to cover the protective ring and the chip. The protective ring is disposed between the pad and the chip, which can disperse the force, improve a force-cushioning effect and protect the chip, so as to reduce a foreign body sensation and prolong the service life of the chip.

6 Claims, 4 Drawing Sheets

CHIP PAD DECOMPRESSION STRUCTURE

FIELD OF THE INVENTION

The present invention relates to a chip pad, and more particularly to a chip pad decompression structure.

BACKGROUND OF THE INVENTION

The wrapping and retaining structure of a conventional chip unit comprises a retaining film. The retaining film is configured to wrap a plurality of chips to form a chip unit, so that the chip unit is completed. When in use, the chip unit cooperates with a close-fitting accessory, such as a belt. When the close-fitting accessory is attached to the user's body, the chip unit will emit far-infrared rays to the user's body. Far-infrared rays radiate a small amount of energy to the user's body and are resonantly absorbed by water molecules in the user's body, thereby generating deformation vibrations to promote blood circulation and enhance metabolism.

However, if the chip unit is used, in cooperation with a foot pad, on the foot of the user, the weight of the user will be concentrated on the chip. When the user moves or walks, he/she may have a foreign body sensation. The user feels uncomfortable. Besides, it will cause deformation or damage to the chip unit, which will reduce the effect of the product greatly. Accordingly, the inventor of the present invention has devoted himself based on his many years of practical experiences to solve these problems.

SUMMARY OF THE INVENTION

The primary object of the present invention is to provide a chip pad decompression structure, which can improve a force-cushioning effect and protect a chip, so as to reduce a foreign body sensation and prolong the service life of the chip.

In order to achieve the above object, the chip pad decompression structure provided by the present invention comprises a pad, a protective ring, a chip, and an upper lid. The pad has a recess. The protective ring is disposed in the recess of the pad. The protective ring has a through hole. The chip is disposed in the through hole of the protective ring. The upper lid is configured to cover the protective ring and the chip.

In the chip pad decompression structure provided by the present invention, the protective ring is disposed between the pad and the chip, which can disperse the force, improve a force-cushioning effect and protect the chip, so as to reduce a foreign body sensation and prolong the service life of the chip.

DETAILED DESCRIPTION OF THE PREFERRED EMBODIMENTS

Embodiments of the present invention will now be described, by way of example only, with reference to the accompanying drawings.

Figure 1:
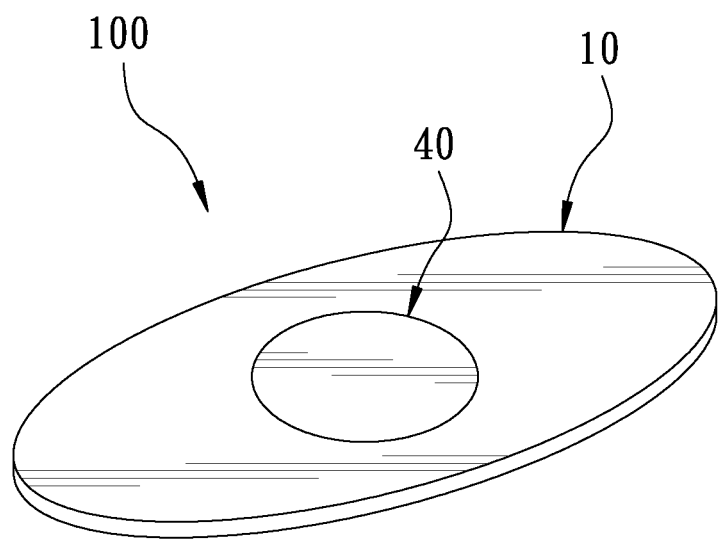
FIG. 1 is a perspective view in accordance with a preferred embodiment of the present invention.
Figure 2:
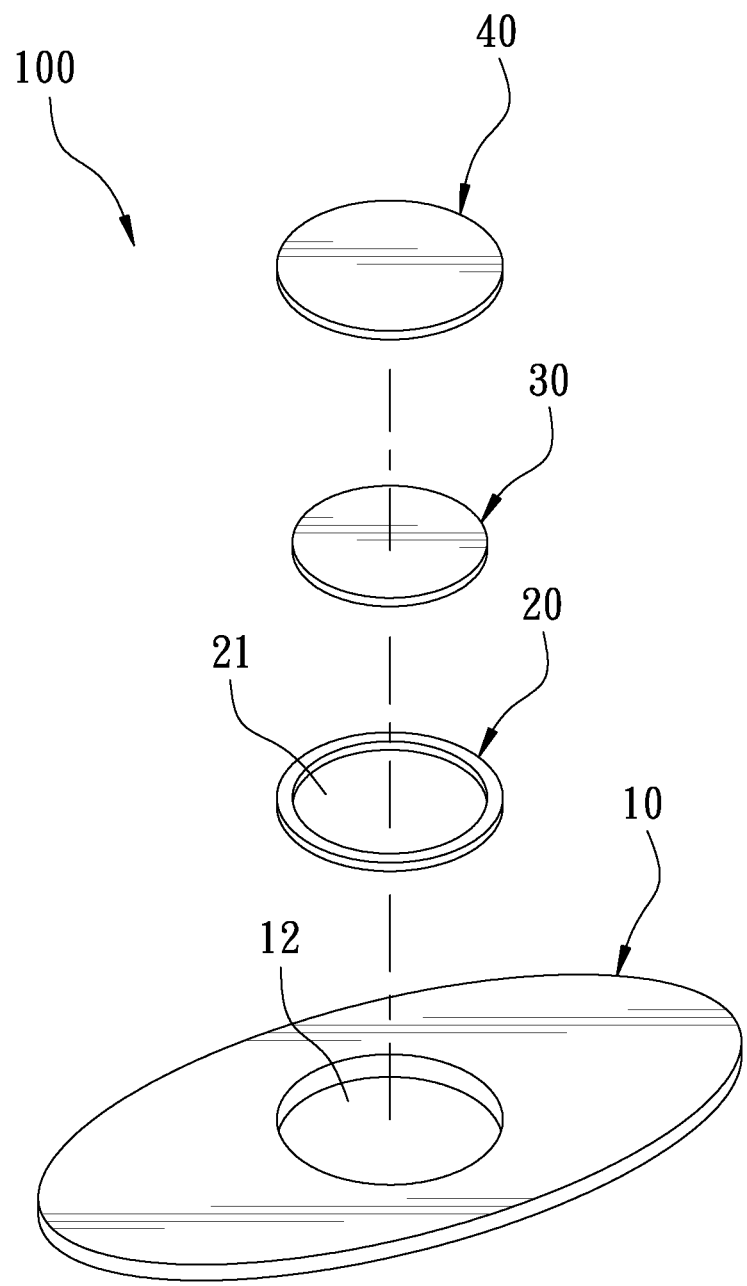
FIG. 2 is an exploded view in accordance with the preferred embodiment of the present invention.
Figure 3:
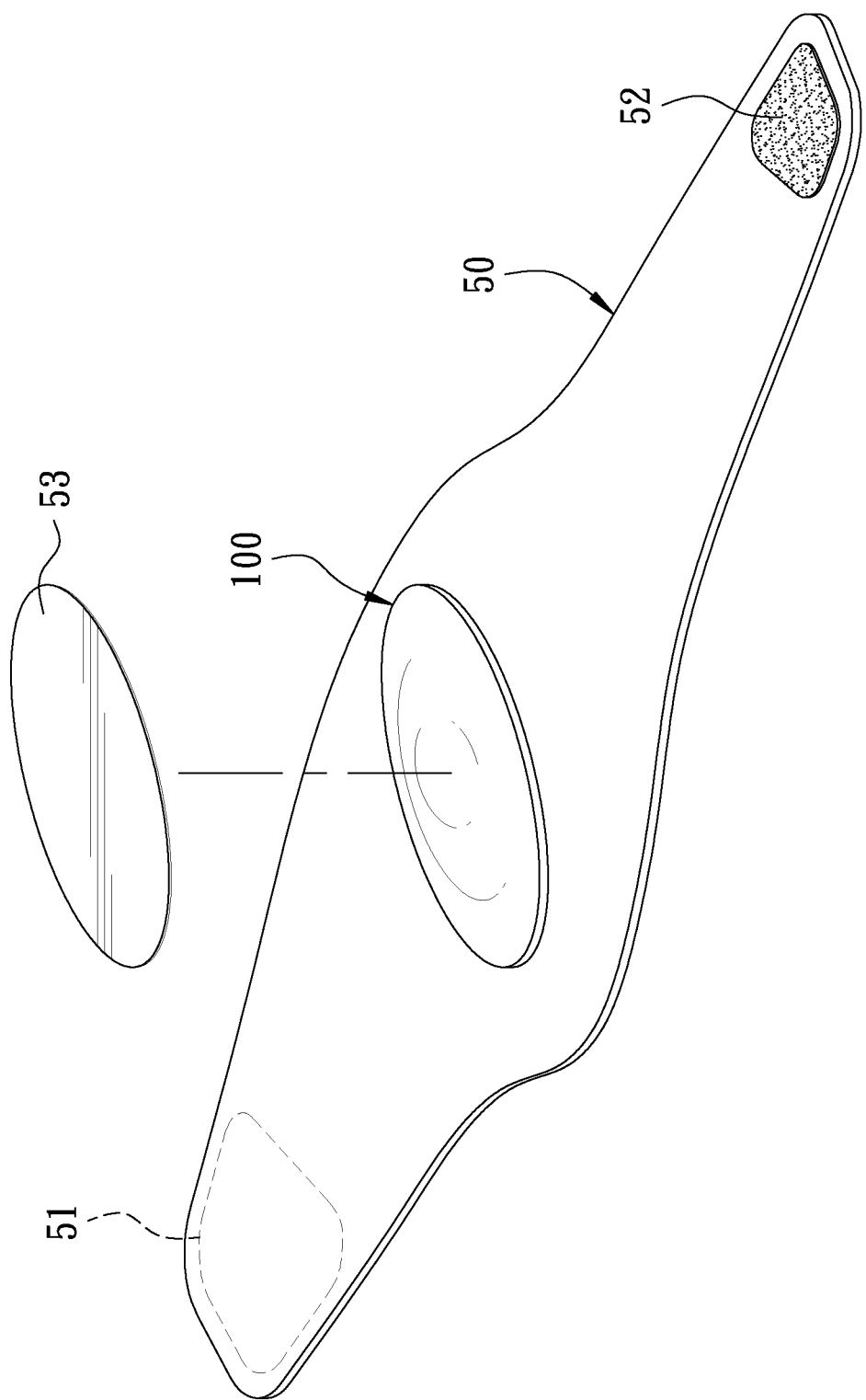
FIG. 3 is a schematic view in accordance with the preferred embodiment of the present invention, illustrating that the chip pad decompression structure is joined to the strap.

FIG. 1 is a perspective view in accordance with a preferred embodiment of the present invention. FIG. 2 is an exploded view in accordance with the preferred embodiment of the present invention. FIG. 3 is a schematic view in accordance with the preferred embodiment of the present invention. The present invention discloses a chip pad decompression structure 100, comprising a pad 10, a protective ring 20, a chip 30, and an upper lid 40.

Figure 4:
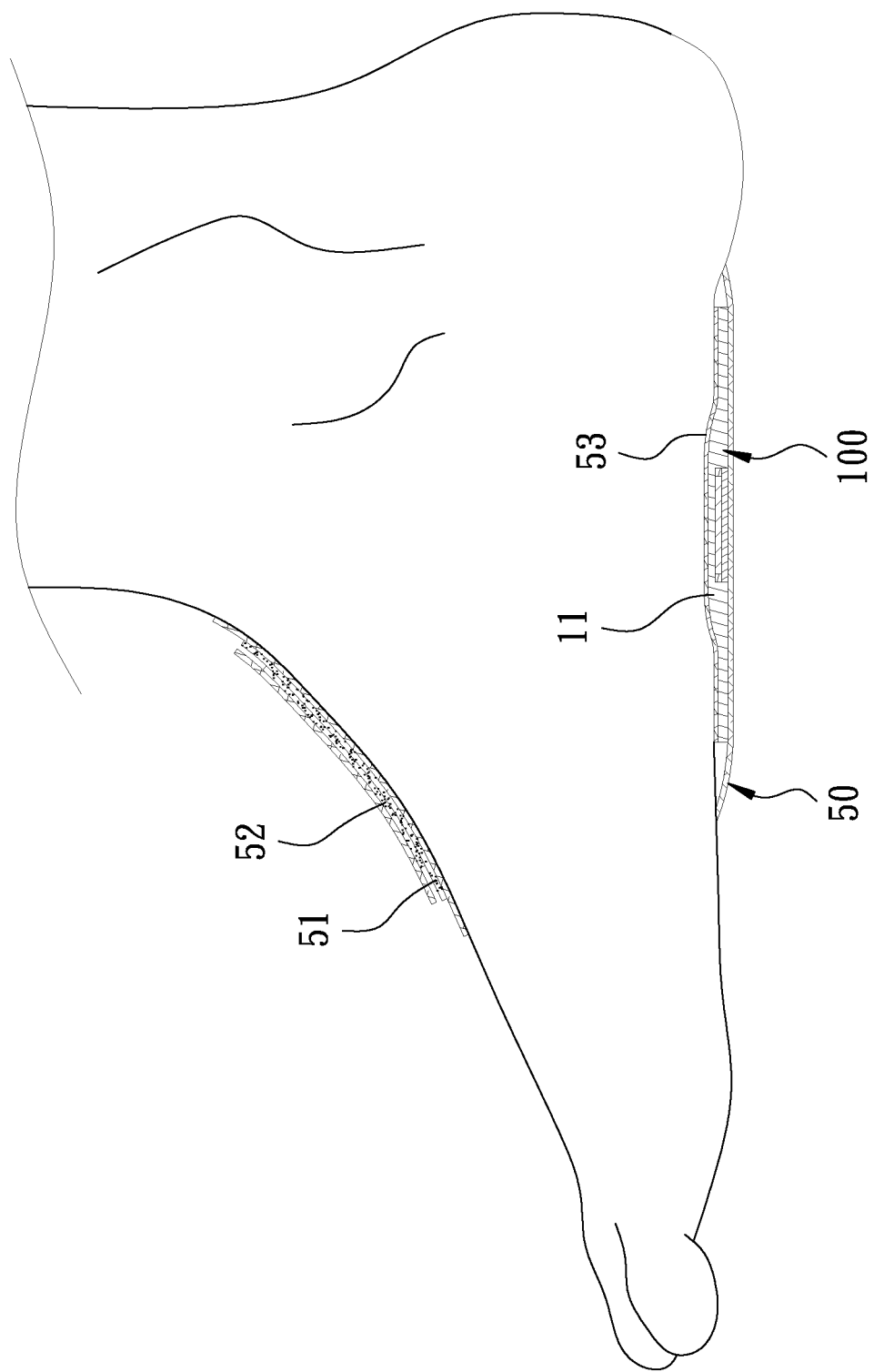
FIG. 4 is a schematic view in accordance with the preferred embodiment of the present invention when in use.

In this embodiment of the present invention, the material of the pad 10 is silicone. The pad 10 has a hardness of Shore A 28. The shape of the pad 10 may be round or oval, but not polygonal with acute angles. In this embodiment, the shape of the pad 10 is oval. The middle of one side of the pad 10 has a raised portion 11. As shown in FIG. 4, the thickness of the middle of the raised portion 11 is greater than the thickness of the periphery of the raised portion 11, so that the cross-section of the raised portion 11 has a trapezoid-like shape. The other side of the pad 10 has a recess 12. The recess 12 is a round recess. The bottom of the recess 12 corresponds in position to the raised portion 11.

The protective ring 20 is disposed in the recess 12 of the pad 10. The protective ring 20 has a through hole 21. The hardness of the protective ring 20 is greater than that of the pad 10. In this embodiment of the present invention, the material of the protective ring 20 is silicone. The protective ring 20 has a hardness of Shore A 50. The shape of the protective ring 20 may be round or oval, but not polygonal with acute angles. In this embodiment, the shape of the protective ring 20 is round.

The chip 30 is disposed in the through hole 21 of the protective ring 20 and is located in the recess 12 of the pad 10. The chip 30 includes a metal substrate. The metal substrate may be one of iron, zinc and aluminum, and has thermal conductivity. The surface of the metal substrate is sprayed with a coating. The coating is composed of materials such as germanium, carbon, calcium, silica, oxygen and adhesives mixed in proportion, enabling the chip 30 to increase in temperature due to the body temperature and to emit far-infrared radiation energy. The shape of the chip 30 may be round or oval, but not polygonal with acute angles. In this embodiment, the shape of the chip 30 is round.

The upper lid 40 is configured to cover the protective ring 20 and the chip 30. In this embodiment of the present invention, the material of the upper lid 40 is silicone. The upper lid 40 has a hardness of Shore A 28. The shape of the upper lid 40 may be round or oval, but not polygonal with acute angles. In this embodiment, the shape of the upper lid 40 is round.

The chip pad decompression structure 100 is arranged on a strap 50. The strap 50 includes a first connecting portion 51 and a second connecting portion 52 at both ends thereof. In this embodiment of the present invention, the first connecting portion 51 and the second connecting portion 52 are hook-and-loop fasteners, so that the first connecting portion 51 and the second connecting portion 52 can be adhered to the opposing surfaces to be fastened. The strap 50 further includes a fabric 53. The fabric 53 is suede fabric. The fabric 53 is configured to cover the chip pad decompression structure 100. The fabric 53 is joined to the strap 50 by high frequency welding, so that the chip pad decompression structure 100 is secured to the strap 50.

Referring to FIG. 2 and FIG. 3, when the chip pad decompression structure 100 of the present invention is to be assembled, the pad 10 is first turned upside down so that the recess 12 of the pad 10 faces upward. The protective ring 20 is placed into the recess 12, and then the chip 30 is placed into the through hole 21, so that both the protective ring 20 and the chip 30 are located in the recess 12. The upper lid 40 is glued to cover the protective ring 20 and the chip 30, so that the protective ring 20, the chip 30 and the upper lid 40 are secured to the pad 10 to complete the assembly of the chip pad decompression structure 100. The chip pad decompression structure 100 is joined to the strap 50. The strap 50 is on one side of the pad 10 opposite to the upper lid 40. The fabric 53 is configured to cover one side of the pad 10 opposite to the raised portion 11. The fabric 53 is joined to the strap 50 by high frequency welding. The strap 50 may be worn on the neck, hand, wrist, or arch of the foot, forefoot, and heel of the feet and other body parts of the user.

FIG. 4 is a schematic view in accordance with the preferred embodiment of the present invention when in use. In this embodiment, the chip pad decompression structure 100 is used on the arch of the user's foot. The chip 30 increases in temperature due to the body temperature and emits far-infrared rays. Far-infrared rays can penetrate the skin of the user and resonate with the water that accounts for 65%-70% of the user's body, making the water change from large molecules to small molecules and generating heat via intermolecular friction. The subcutaneous temperature rises via the heat reaction, which can promote the expansion of microvessels, accelerate blood circulation, promote metabolism, and remove harmful substances and heavy metals in the user's body. Thus, new enzymes are rapidly produced to activate cells, such that the physiological functions of the user's body are more active, and the immunity is improved to resist diseases.

It is worth mentioning that when the user's foot treads on the chip pad decompression structure 100, the raised portion 11 will cushion the force. The protective ring 20 is disposed between the pad 10 and the chip 30, which can further disperse the force to the whole pad 10, reduce the phenomenon of uneven distribution of the force, and improve a force-cushioning effect. The compressive force can be reduced and the chip 30 can be protected when in use, so as to reduce a foreign body sensation and prolong the service life of the chip 30.

What is claimed is:

1. A chip pad decompression structure, comprising:
   a pad, the pad having a recess;
   a protective ring, disposed in the recess of the pad, the protective ring having a through hole;
   a chip, disposed in the through hole of the protective ring;
   an upper lid, configured to cover the protective ring and the chip;
   wherein the pad, the protective ring, and the upper lid are made of silicone:
   wherein the pad and the upper lid each have a hardness of Shore A 28;
   and wherein the protective ring has a hardness of Shore A 50.

2. The chip pad decompression structure as claimed in claim 1, wherein the protective ring has a hardness greater than that of the pad.

3. The chip pad decompression structure as claimed in claim 1, wherein the pad, the protective ring, the chip and the upper lid each have a round or oval shape.

4. The chip pad decompression structure as claimed in claim 1, wherein the pad has an oval shape, and the protective ring, the chip and the upper lid each have a round shape.

5. The chip pad decompression structure as claimed in claim 1, wherein a middle of one side of the pad has a raised portion, another side of the pad has the recess, and a bottom of the recess corresponds in position to the raised portion.

6. The chip pad decompression structure as claimed in claim 1, wherein the pad is connected to a strap, the strap includes a first connecting portion and a second connecting portion at two ends thereof, the first connecting portion and the second connecting portion are fastened to each other.

* * * * *